（12）United States Patent
Thyagarajan et al.

(10) Patent No.: US 11,426,599 B2
(45) Date of Patent: Aug. 30, 2022

(54) THREE-DIMENSIONAL COIL SET USED FOR NEUROMODULATION

(71) Applicant: Palo Alto Research Center Incorporated, Palo Alto, CA (US)

(72) Inventors: Krishnan Thyagarajan, Mountain View, CA (US); Bernard D. Casse, Saratoga, CA (US); Christopher Paulson, Livermore, CA (US); George Daniel, Palo Alto, CA (US); Armin R. Volkel, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 209 days.

(21) Appl. No.: 16/692,639

(22) Filed: Nov. 22, 2019

(65) Prior Publication Data

US 2021/0154488 A1   May 27, 2021

(51) Int. Cl.
*A61N 2/02* (2006.01)
*A61N 2/00* (2006.01)

(52) U.S. Cl.
CPC ............... *A61N 2/02* (2013.01); *A61N 2/006* (2013.01)

(58) Field of Classification Search
CPC .................................. A61N 2/006; A61N 2/02
See application file for complete search history.

(56) References Cited

U.S. PATENT DOCUMENTS

| 8,788,064 | B2 | 7/2014 | Mercanzini et al. |
|---|---|---|---|
| 9,108,041 | B2 | 8/2015 | Craig |
| 9,254,383 | B2 | 2/2016 | Simon et al. |
| 2010/0185042 | A1 | 7/2010 | Schneider et al. |
| 2010/0249577 | A1 | 9/2010 | Schneider |
| 2019/0028285 | A1 | 9/2019 | Thayagarajan et al. |

FOREIGN PATENT DOCUMENTS

| AU | 2008352005 | 9/2009 |
|---|---|---|
| WO | 2009/026386 | 2/2009 |

OTHER PUBLICATIONS

U.S. Appl. No. 16/235,634, filed Dec. 28, 2018, Thayagarajan.
European Search Report from EP Application No. 20207055.3 dated Apr. 14, 2021, 6 pages.

*Primary Examiner* — Christine H Matthews
(74) *Attorney, Agent, or Firm* — Mueting Raasch Group

(57) ABSTRACT

A neuromodulator includes one or more coil sets. Each of the coil sets has three coils aligned to produce magnetic and electric fields in three different directions. A plurality of conductors couple the coils of the one or more coil sets to one or more input signals such that each of the coils is independently activated via an individually selectable current applied through the conductors. The individual activation creates a resultant field that is a combination of the magnetic and electric fields in three different directions for each of the coil sets.

20 Claims, 9 Drawing Sheets

THREE-DIMENSIONAL COIL SET USED FOR NEUROMODULATION

SUMMARY

The present disclosure is directed to a three-dimensional coil set used for neuromodulation. In one embodiment, a neurostimulation system and apparatus include one or more coil sets. Each of the coil sets has three coils aligned to produce magnetic and electric fields in three different directions. A plurality of conductors couple the coils of the one or more coil sets to one or more input signals such that each of the coils is independently activated via an individually selectable current (and other properties of the current including but not restricted to phase, amplitude and frequency) applied through the conductors. The individual activation creates a resultant field that is a combination of the magnetic and electric fields in the three different directions for each of the coil sets.

In another embodiment, a method involves independently applying three or more individually selectable currents (and other properties of the current including but not restricted to phase, amplitude and frequency to three or more coils aligned to produce magnetic and electric fields in at least three different directions. In response to the application of the currents, a resultant field is created that is a combination of the magnetic and electric fields in three different directions for each of the coil sets. The resultant field is applied to neuromodulate organic tissue.

These and other features and aspects of various embodiments may be understood in view of the following detailed discussion and accompanying drawings.

BRIEF DESCRIPTION OF THE DRAWINGS

The discussion below makes reference to the following figures, wherein the same reference number may be used to identify the similar/same component in multiple figures. The drawings are not necessarily to scale.

DETAILED DESCRIPTION

Figure 1:
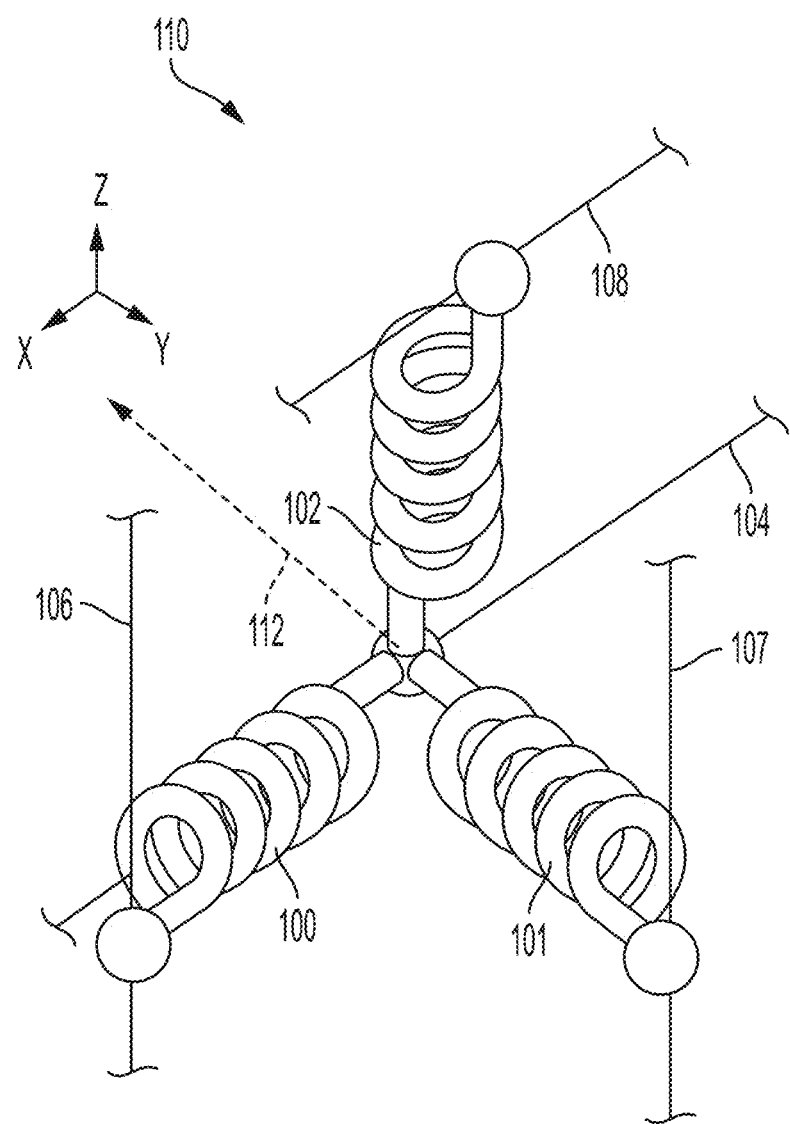
FIG. 1 is a perspective view of a coil set according to an example embodiment.

The present disclosure relates to methods and apparatuses used for neuromodulation. Neuromodulation involves using electric or magnetic fields to stimulate nerves to alter nerve activity (excite/stimulate or suppress/inhibit), and is an emerging therapy for treatment of a broad range of diseases and conditions as well as for augmenting the functioning of the human brain. For example, neuromodulation has the potential to provide important and life changing therapy for intractable pain, spinal cord injuries, headaches, Parkinson's disease, Alzheimer's disease, depression, and many other afflictions.

Magnetic modulation is currently a primary noninvasive method for delivering neuro-stimulatory and neuro-suppressant pulses to the human brain and can be used for other kinds of magnetic stimulation of neural tissue in other regions of the body as well. However, the degree of control possible with conventional magnetic stimulation using single coils is greatly limited by the fact that the field with a given coil is cannot be spatiotemporally shaped in near real-time.

Our ability to gain a good understanding of brain response and functioning as well as the neural response and circuitry of other regions of the body is currently limited by the restricted ability for non-invasive probing and stimulation. Transcranial Magnetic Stimulation (TMS) is the most frequently used noninvasive method in the market and allows pulsed sub-millisecond control, however it is limited by the fact that the coil is fixed in position and at most can only be moved manually, which gives it poor precision and limited interrogation capabilities. Transcranial Alternating Current Stimulation (tACS), another technique involves the use of electrodes touching the scalp and has its own limitations in depth of stimulation as well as amount of current permitted to be safely utilized. In addition, continuous wave stimulation is currently restricted due to heating issues and inability to control the spatiotemporal fields, which in turns dissipates energy In embodiments described below, coil arrangements, geometry and materials are utilized for highly improved localized electromagnetic field distribution control. Such implementations use electromagnetic beam steering and require no mechanically moving parts. Using advanced phase and amplitude control over the currents in the coils, the generated electromagnetic fields can be modified to ensure constructive and destructive interference of the fields inside organic/biological tissue. Closed-loop controls in both the spatial and temporal aspects of the electromagnetic field being delivered, can be an effective means to stimulate various regions of neural tissue.

An array of multi-coil or multi-channel coil architecture can use an arrangement of three-dimensional (3-D) coils in a 3-D geometry (motif), that permits deeper penetration of the magnetic fields, additionally so when used with material systems with high magnetic permeability, in the core. Today, there is not a functional hardware prototype with more than a four-element array, and that array is on a single plane. This is due to a multitude of design limitations, including uncompensated mutual coupling between coils, incorrect current distributions, need for different current sources for each of the coils, limitations in planar coil shapes, and a lack of optimization algorithms.

The technology described herein, which was developed to address prior limitations of TMS and other noninvasive electromagnetic stimulation uses an array of electromagnetic radiators. By tailoring the phase shifts and intensities of each element in a phased array, individual wave fronts from each radiator are superimposed to create constructive and destructive interference, yielding collimated and steered beams, with much lower mutual coupling and mutual inductance between the individual elements. In addition, the arranged geometry permits the use of cooling techniques (e.g., fluid based), that will enable operations with long endurance.

The coil array platform includes of an array of individually-addressable coils but tailored for controllable constructive or destructive addition of fields. By controlling the amplitude and phase of the current in each coil, the array yields magnetic fields with a wide array of spatial distributions that can be made to mimic and tap into the various modes of brain excitation (alpha waves, theta bursts, beta waves etc.). By dynamically altering the current intensities in each coil with appropriate weightings we can also achieve spatial and temporal field steering. This enables more precise delivery of stimulation to the target areas of interest, as well as dynamic adaptation to maximize downstream neural stimulation effects and customize the treatment for different patients. This can be important since the physical morphology of the brain and skull varies from patient to patient.

A treatment device described herein makes use of 3-D coils in 3-D arrangements. There are three advantages of utilizing these 3-D coil geometries instead of 2-D coils: 1) they have more degrees of freedom in 3-D space, resulting in greater control of electromagnetic (EM) fields over conventional flat coils, 2) the coils can carry lower current compared to planar geometries, and 3) further reduction of currents can be achieved by embedding high-permeability material within the coils, giving the ability to control the spreading of the fields.

As each coil will be driven by a current controlled power amplifier, hundreds of amps of current can be applied by stacking multiple power supply boards together. Moreover, since the amplifiers are controlled by a digital to analog converter (DAC) that provides inputs in the hundreds to thousands of Hertz, this allows us full control over the stimulation delivered, allowing both traditional pulse-based stimulation and continuous stimulation waveforms.

In FIG. 1, a perspective view shows a set 110 of coils 100-102 that can be used in devices, systems, and methods according to example embodiments. Generally, a neuromodulator (also referred to herein as neurostimulator or neurosuppressor) apparatus and system may use multiple sets 110 of coils, wherein each set includes three or more coils oriented in different directions. In other embodiments, the sets may include coils grouped together all having the same orientation, wherein different sets have different orientations. An example of this latter configuration will be shown further below. No matter how the coils are arranged into sets, in a particular area or volume of the apparatus, there may be at least three coils of differing orientation such that activation of the individual coils will cause a resultant magnetic field to be emitted from the area or volume.

In the example of FIG. 1, the coils 100-102 in the set 110 are orthogonal to each other, being aligned with the x, y, and z axes, respectively. By varying the amplitude and direction of a current passing through the coils 100-102, a resultant the magnetic field produced by the coils 100-102 can be directed to any direction in 3-D space. The magnitude of the resultant field can also be controlled based on the combination of the individual field strengths. Note that coils sets with non-orthogonally oriented coils may also be used in some embodiments described below. Also note that in some cases, a coil set may include two or more coils that produce fields in just two directions, but can be otherwise configured to work similarly to the sets with fields in three directions as described herein. Also consider that if two coils are aligned to the same axis but produce fields in different directions, this might also be considered producing a electric and magnetic fields in different directions. In most cases shown below, the three fields are shown at three different angles in 3-D space relative to a reference.

The currents applied to the coils 100-102 are delivered by a plurality of conductors 104, 106-108 that couple the coils 100-102 to one or more input signals. In this example, conductor 104 is a common line coupled to one side of all of the conductors 100-102. The other sides of each coil 100-102 are coupled to separate, individually controlled lines 106-108. In this embodiment, the common conductor 104 may be held at a zero volt electrical potential (e.g., ground) and the other conductors 106-108 can vary between a positive and negative voltage relative to ground. There are other ways to couple individual sets of coils, and some alternatives will be described below.

Generally, a set of coils as shown in FIG. 1 can provide a resultant magnetic field 112 that is a combination of the individual magnetic fields in three different directions generated by each coil 100-102 the coil set. The direction and magnitude of the resultant field can be dynamically varied in both direction and magnitude. Multiple coil sets can be included in a single device, and the resultant field from each set can be combined to produce a field that varies in three-dimensional space within a target volume. The size of the target volume is only limited by the size of the coils and size of the device that holds the coil sets but may also be influenced by the current running through the coils themselves. For neuromodulation, the coil size may be centimeter-scale and the target volume can range from 1.5-5 $mm^3$, although smaller or larger volumes may be targeted for this and other applications.

Figure 2:
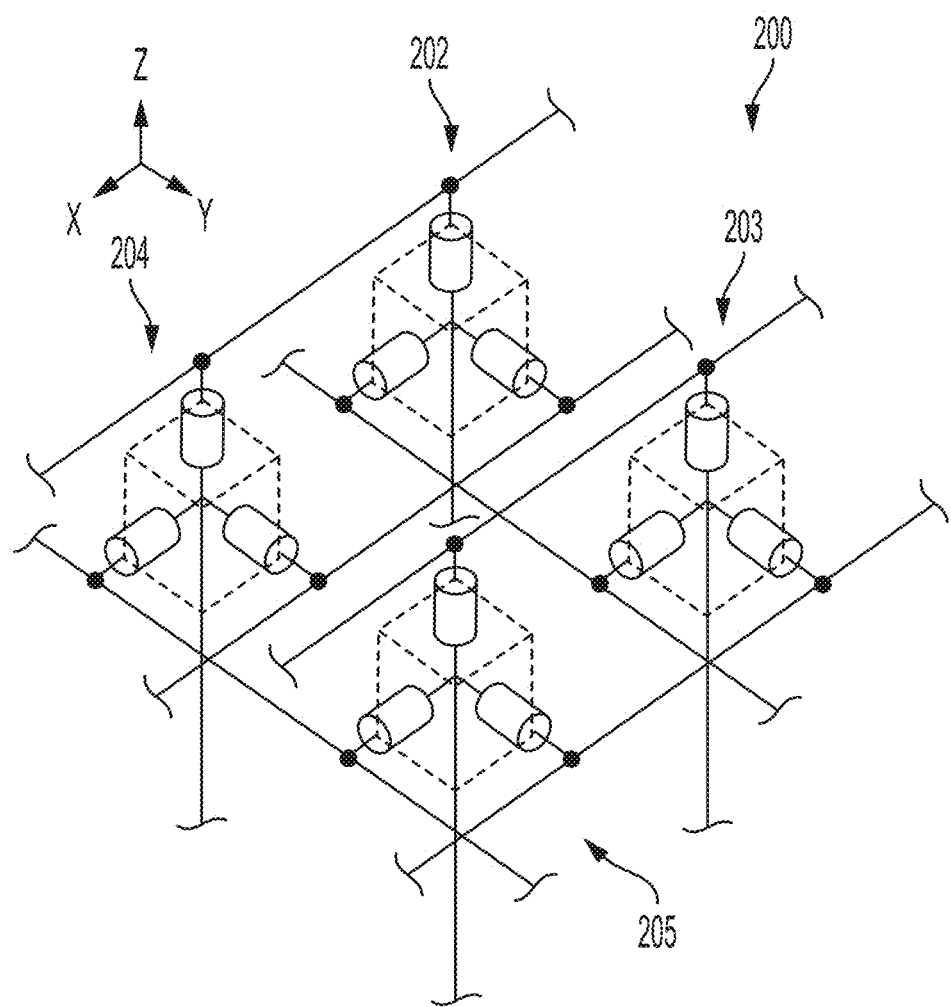
FIG. 2 is a diagram showing the connection of multiple coil sets according to an example embodiment.

In FIG. 2, a perspective view schematically shows an array 200 of coil sets 202-205 according to an example embodiment. The cuboid drawn in dashed lines in each set 202-205 generally indicates that each set 202-205 may be considered a separate magnetic field generator whose field originates generally within the cuboid. Although each coil could be individually wired, with a dedicated supply and dedicated or common return line, this example uses a switching matrix to reduce the number of signal lines. Such a switching matrix may be used if it allows the system to achieve certain baseline specifications, e.g., related to row/column scanning times and electrical storage capacity coupled to the coils. For example, in order to meet metrics for a certain kind of treatment, large currents could be needed which may involve storing significant amounts of charge, e.g., using large capacitors. Thus, the ability to utilize a matrix/switching architecture may be dictated by the target ramp up or ramp down times of the coil elements.

The conductors shown this figure are indicated as being either part of rows (e.g., $R_{X1}$) or columns ($C_1$). As will be described in detail below, this is one way to reduce the number of lines needed to activate individual coils within the sets. By using a current blocking/switching device (not shown) such as a transistor in series with the coils, individual coils can be activated by applying a voltage across its row and column conductors that allows current to flow through the current blocking device (e.g., forward biasing), while other coils that are to be deactivated by applying a different voltage (e.g., reverse biasing) to one of its current blocking devices via the row and column lines of the deactivated coils.

Figure 3:
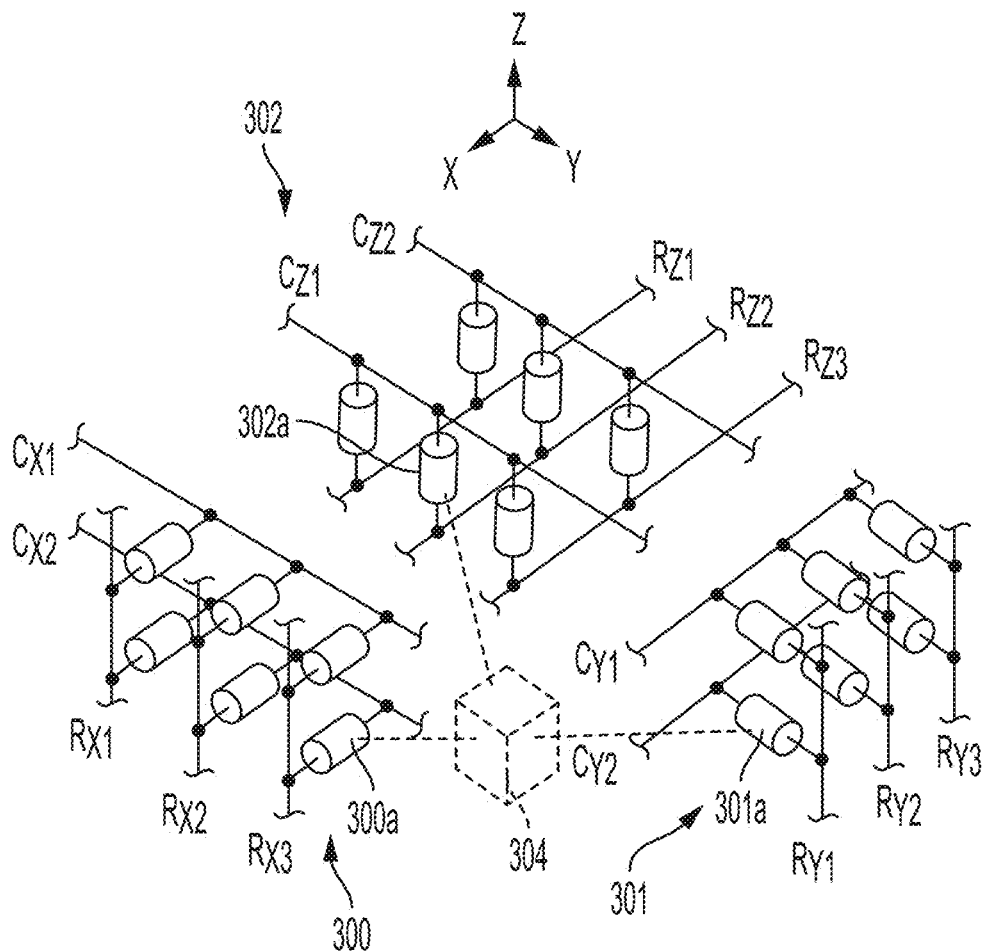
FIG. 3 is a diagram showing the connection of multiple coil sets according to another example embodiment.

Note that in the embodiments above, the coils sets were shown with three orthogonally oriented coils coupled together, e.g., tied to a common return line. There may be other arrangements having at least three coils aligned to produce magnetic fields in three different directions where the coils in each set are not tied together electrically. The diagram in FIG. 3 shows another arrangement of coil sets according to an example embodiment where the coils in each set are not electrically coupled.

Groups 300-302 of coils include a plurality of coils wired together and oriented in the respective x-, y-, and z-directions. While the groups 300-302 are shown in the drawing having physically proximate coils, this is for purposes of clarity in the drawings showing the electrical connections and the individual coils could be oriented much differently. Generally, the physical arrangement of individual coils can be such that a particular volume has at least one coil from each group 300-302. For example, coils 300a, 301a, and 302a may be physically located within volume 304 as indicated by the dashed lines. So, although the coils 300a, 301a, and 302a may not share any common electrical lines, they can still be activated together to cause the desired resultant field emanating from volume 304.

Figure 4:
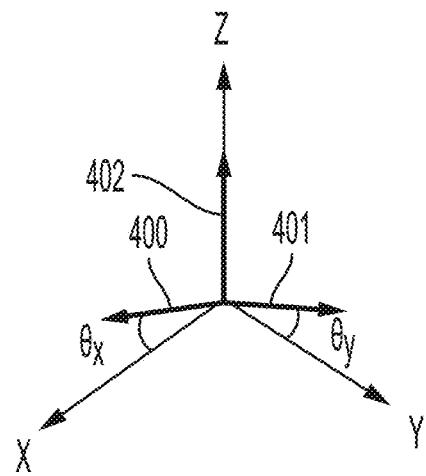
FIG. 4 is an diagram showing non-orthogonal fields according to an example embodiment.

Using orthogonal coils in each coil set may provide some advantages, e.g., having the widest coverage in three-dimensional space. In some cases, however, it may be possible or desirable to use non-orthogonally oriented coils. For example, FIG. 4 is a plot showing individual field orientations 400-402 of three coils of a coil set according to an example embodiment. The z-field 402 is aligned with the z-axis, but the other two fields 400, 401 are not aligned with the x- and y-axes. Field 400 is aligned with the xz-plane and offset from the x-axis by angle $\theta_x$. Field 401 is aligned with the yz-plane and offset from the y-axis by angle $\theta_y$. Such an arrangement may be used to provide stronger fields in the z-direction than would be possible with equivalent coils that are orthogonal. This would be additionally advantageous to access certain regions of the brain whose orientation may need directional and non-orthogonal neuromodulation. This may be useful in a treatment device 500 according to an example embodiment shown in FIG. 5.

The treatment device 500 includes a treatment surface 502 that may be applied transcutaneously for treatment of organic tissue. A coil array 504 is embedded below the surface 502, each element of the coil array 504 having a coil set as described above. If the coils are arranged so that fields emanate, e.g., as shown in FIG. 4, then the net field of the device 500 could be biased to increase the relative field strength in the z-direction than if the non-z-oriented coils were orthogonal to the z-direction.

Figure 5:
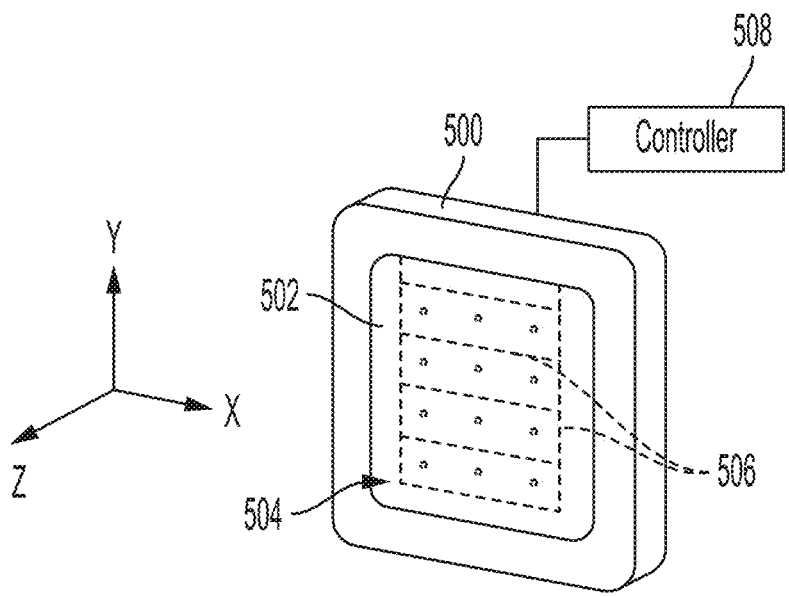
FIG. 5 is a perspective view of a treatment device according to an example embodiment

Also shown in FIG. 5 are heat sinks 506 that may be placed between individual coil sets of the array 504. The heat sinks 506 may include solid materials (e.g., copper, gold) with high thermal conductivity and may include fluid channels that circulate a coolant around the array 504. The separation of the coils/coils sets in the array 504 allows the heat sinks 506 to be placed between the individual coils and may include additional paths not shown, e.g., oriented in the y-direction around columns of the array 504. Heat sink structures may also be placed between the coil array 504 and the treatment surface 502 assuming such structures do not interfere with the magnetic fields emanating from the array. Heat sink structures may also be placed behind the array 504 facing away from the treatment surface 502. Generally, the heat sinks 506 will be thermally coupled to a heat transfer device (e.g., radiator) that transfers the heat to ambient air or some other heat reservoir (e.g., fluid reservoir).

The coil arrangements and control circuitry that drives them allows spatial and temporal control of the magnetic stimulation field. This can be enabled by shaping magnetic and induced electric fields using constructive/destructive interference between the fields from multiple coils, guided by electric field simulations and closed-loop feedback from resulting responses, and development of a novel stimulator design capable of pulse and continuous oscillatory stimulation. The technology is underpinned by an array of three-dimensional (3D) centimeter-scale coils, driven by amplitude-controlled currents (examples of certain kinds of coils include those shown in FIG. 6). This technology may be used for spatiotemporally precise and adaptive neural network modulation.

The electromagnetic stimulation technology can be understood from EM theory: a time varying magnetic field will induce an electric field as described by Maxwell's equation $$\frac{\partial \vec{B}}{\partial t} = -\nabla \times \vec{E}.$$

While the skull provides an effective barrier against the penetration of electric fields, magnetic fields at a few kHz can reach up to 2-3 cm deep. In EM theory, the magnetic field created by a loop increases with the radius of the loop, R, and the intensity of the current, i(t), and decreases with the distance, z, along the axis, as shown in Equations (1)-(3) below.

$$H_z^{LOOP}(z) = \frac{\frac{1}{2}R^2 i(t)}{(R^2+z^2)^{3/2}} \quad (1)$$

$$H_z^{COIL}(z) = \frac{i(t)}{4\pi r \tan\alpha} \left\{ \frac{N\pi r \tan\alpha + z}{\sqrt{r^2 + (N\pi r \tan\alpha + z)^2}} + \frac{N\pi r \tan\alpha - z}{\sqrt{r^2 + (N\pi r \tan\alpha - z)^2}} \right\} \quad (2)$$

$$\tan\alpha = \frac{1}{2\pi N r} \quad (3)$$

Figure 6:
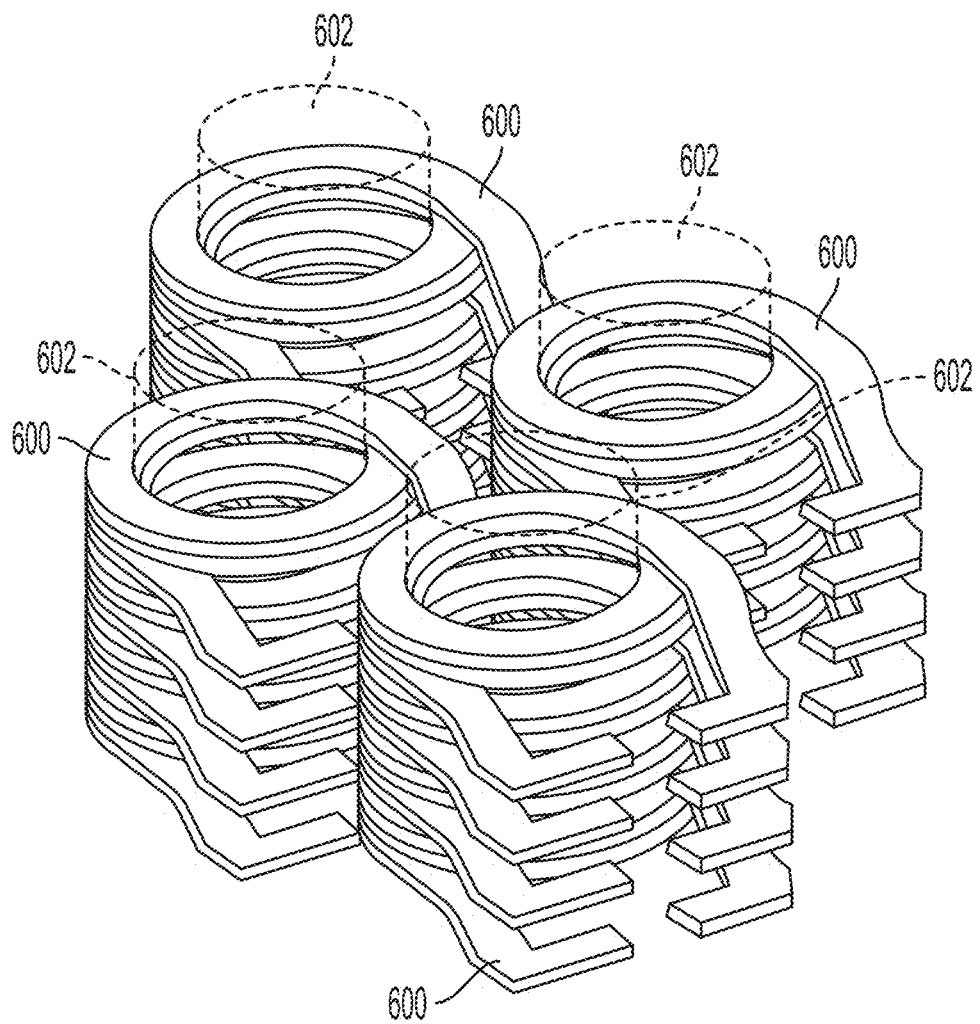
FIG. 6 is a perspective view of a coil array according to an example embodiment.

The magnetic field of a coil depends on the number of turns, N, the length, l, the pitch, $\alpha$, and the amplitude of the current. By increasing N (or the inductance of the coils) and length l, the resulting magnetic field can be increased even while keeping the current and coil radius fixed. By arranging coils in a 3-D shape (e.g. a box-like configuration as seen in FIG. 6), greater flexibility in field shaping can be attained. The induced electric field is then proportional to the first temporal derivative of the magnetic field. Arranging a number of small coils 600 in an array configuration as in FIG. 6, yields an increase in the magnetic field intensity, and thus induced electric field, and penetration to specific regions. Also seen in FIG. 6 are cores 602 that can be used to intensify the magnetic field of each of the coils.

If all coil currents are driven independently, it is possible to manipulate the fields at selected locations by approximately adding the linear vectors of the individual fields. This implies that tailored stimulations can be obtained by selecting appropriate coil array designs, optimal coil size, number of coils, array configuration, and current intensity distribution (including phase considerations). These individual elements are formed with high permeability material (e.g., ferrite cores) providing higher fields and more focused fields with decreased coil currents. This has the advantage of being able to focus the flux of the magnetic field lines along a tighter trajectory, permitting greater directionality and stimulation depth. This will result in much greater control of magnetic field distributions inside the head. Additional exploration of exotic materials such as ytterbium based ceramics and metal films will permit pushing the concentration of field lines in a marked manner.

Figure 7:
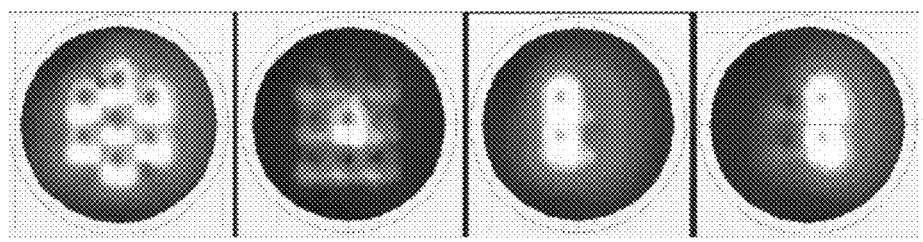
FIGS. 7-10 are plots showing simulation results of a neuromodulator according to an example embodiment.

The ability to steer the beam and hence shape the generated electromagnetic fields provides the capacity to address very specific regions of the brain on demand. Customizable beam steering and field shaping has been demonstrated using simulations of an array of coils with ferrite cores. Such simulations have verified that field-shaping is possible, providing TMS-scale electric fields of 100 V/m at depths of 2.5-3 cm when using currents of the order of 300 A per coil and material with a permeability of 900. The diagram in FIG. 7 shows different field patterns generated at a depth of 2.5 cm by an array of seven coils similar to the set of five coils shown in FIG. 6. The coils are oriented in one direction for this simulation and are demonstrate field patterns created via constructive/destructive interference in a single direction.

The ability to reduce the current requirements (and thus heat generated) comes additionally from material systems made of alloys of iron (Fe), Zinc (Zn) and Manganese (Mn). Such materials can reach permeabilities of greater than 900 (even up to 15,000 for exotic combinations and forms of the materials) permitting very high concentration of magnetic field lines and hence high electric-fields as well. Other attractive features of such materials include good temperature properties such as low losses (loss tangent less than 10-6) and moderate to high Q factors.

Figure 8:
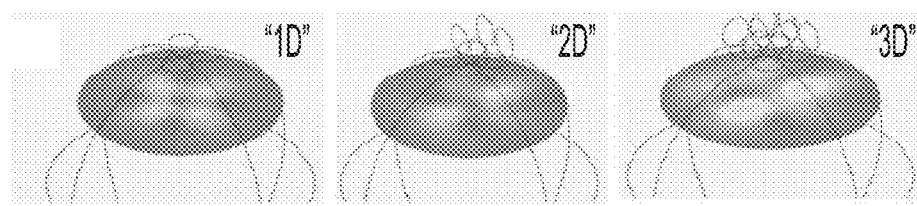

Field plots in FIG. 8 shows simulated field shaping results using 3-D coil arrangements according to example embodiments. In these simulations a 4-coil array for each direction of the 1-D, 2-D, and 3-D generated fields. This shows the ability to generate lower intensity induced electric-fields (few V/m's), for example by running either 100 A or 150 A (at low frequencies, i.e. 10 Hz) in the different coils with different phases. This permits constructive/destructive interference of the fields and gives local low intensity electric-fields, such as needed for continuous stimulation waveforms similar to those used in Transcranial Alternating Current Stimulation (tACS). Changing array arrangement from 1-D (a "floor") to "2-D" (floor and one wall) and to "3-D" (floor and two walls), demonstrates that more complex fields can be applied using a 3-D coil designs.

Figure 9:
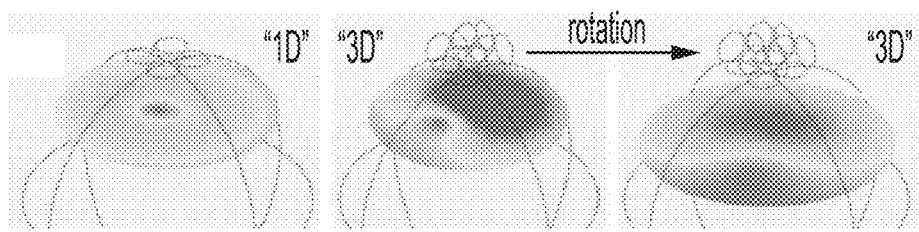

The plots in FIG. 9 show rotating field patterns generated by controlling the phase and amplitude of the currents in the coils. In this example, the fields are generated running higher 300 A currents at higher frequencies (e.g., 4 kHz [250 μs duration] biphasic pulses) through the coils with appropriate phases, generating up to 100 V/m at a depth of 2.5 cm. Note as the induced electric field depends on the rate of change of the magnetic field, slower tACS coils, operating at 300 A and 4 kHz (250 μs duration) pulses and a permeability of 900. Like frequencies naturally result in lower strength fields. As such, only moderately higher currents are needed for 100V/m pulses (4 Hz pulses are faster-changing) versus 1-2V/m continuous lower frequency waveforms.

Figure 10:
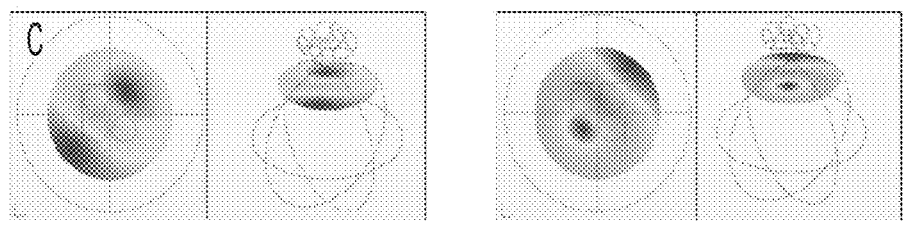

The leftmost image in FIG. 9 shows a planar arrangement at those currents. The middle and rightmost images in FIG. 9 show the same 3-D arrangement with the phase and amplitude of currents controlled to yield a rotation of the fields in time, as is evidenced by the movement in the peak amplitude of the electric field. By differentially energizing and determining the phase of each coil, customizable and unconventional spatial patterns of stimulation can be generated as shown by the plots in FIG. 10.

Figure 11:
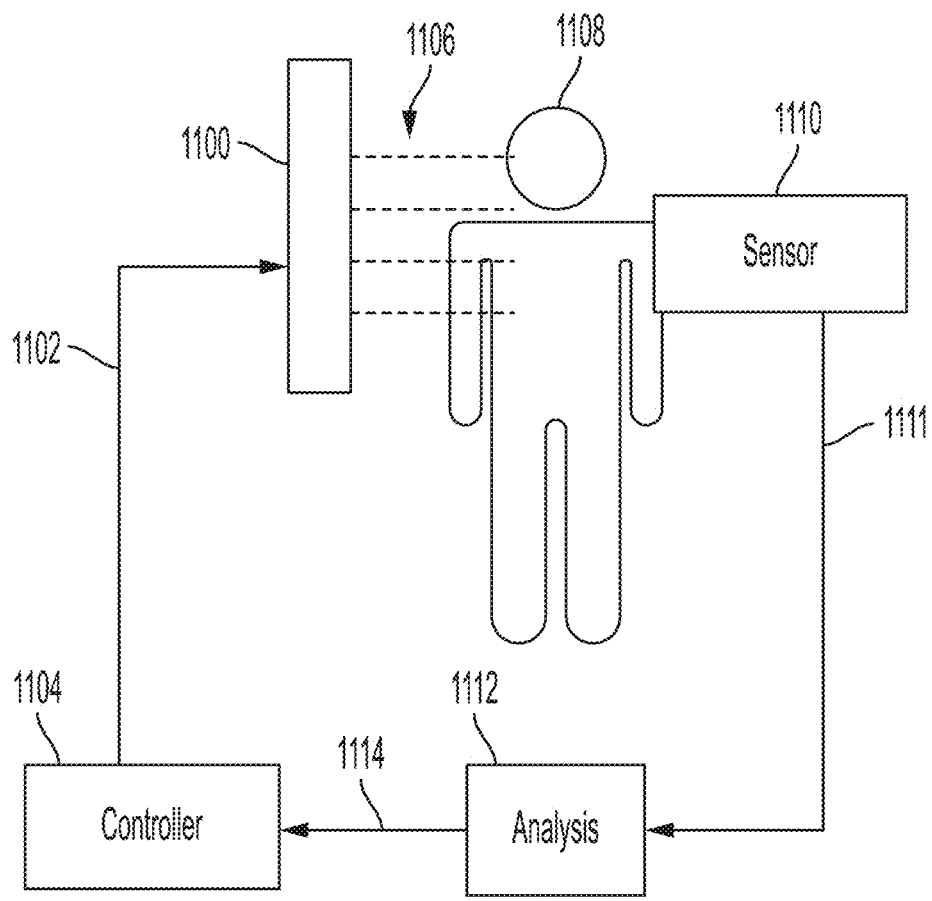
FIG. 11 is a diagram showing a neuromodulator feedback system according to an example embodiment.

As noted above, a closed-loop system may be used to guide the application of 3-D magnetic fields, including shape, direction, strength, etc. of the applied fields. In FIG. 11, a block diagram shows an example of a closed-loop control system according to an example embodiment. A neuromodulation treatment device 1100 receives a control input signal 1102 from a controller 1104 that drive three or more coils within the device 1100. In response to the inputs 1102-1104, the coils output a resultant magnetic field 1106 that can be used for neuromodulation of a patient 1108.

The effect of the field 1106 on the patient is measured and quantified via sensor 1110. The sensor 1110 could utilize magnetic resonance imaging (MRI), functional MRI (fMRI), electroencephalogram (EEG), magnetoencephalography (MEG) etc. which produces a signal 1111 used for analysis device 1112. The sensor 1110 may be located proximate the treatment and measure biological responses such as changes in the material properties of the biological tissue (e.g., temperature, electrical conductivity, chemical balance, etc.) which can be influenced by the electric and magnetic fields.

The analysis device 1112 may be a display or other user interface that allows a clinician to determine the effectiveness of the stimulation. The analysis device 1112 may also have some abilities to deduce relationships between the sensor signals 1111 responsive to the applied fields 1106, and provide suggestions and/or some level of automatic adjustment to achieve a target measurement. A feedback input 1114 is used to re-adjust the controller to ensure that the stimulation achieves or is close to the target response. The feedback input 1114 may be provided manually via a clinician using the analysis device 1112 or a different device, e.g., a user interface coupled to the controller 1104. The feedback 1114 may be applied in real-time and repeatedly adjusted during the treatment of the patient 1108.

Figure 12:
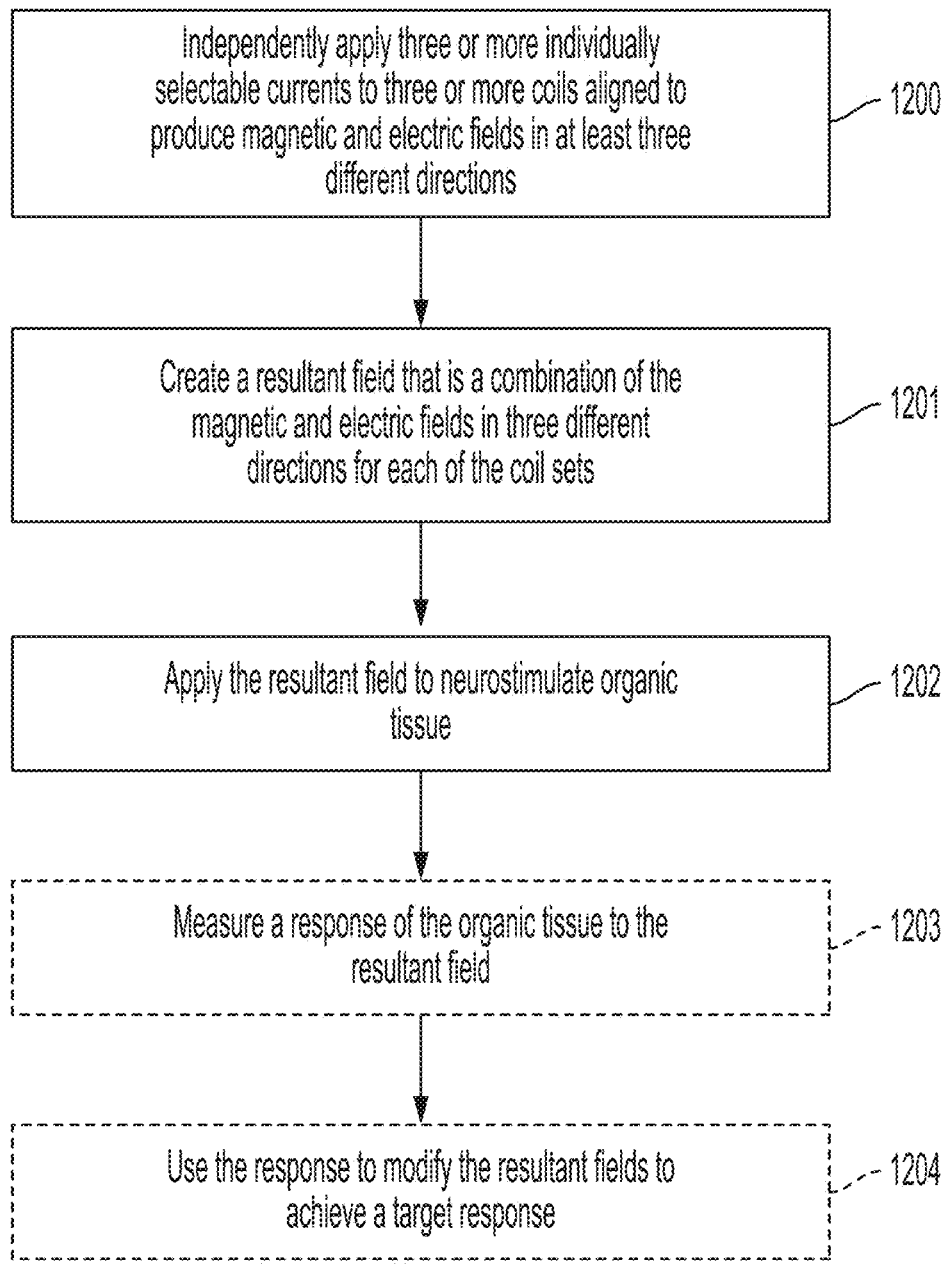
FIG. 12 is a flowchart showing a method according to an example embodiment.

In FIG. 12, a flowchart shows a method according to an example embodiment. The method involves independently applying 1200 three or more individually selectable currents to three or more coils aligned to produce magnetic and electric fields in at least three different directions. In response to the application of the currents, a resultant field is created 1201 that is a combination of the magnetic and electric fields in three different directions for each of the coil sets. The resultant field is applied 1202 to neuromodulate organic tissue. Optionally, the method may also involve measuring 1203 a response of the organic tissue to the resultant field and using 1204 the response to modify the resultant fields to achieve a target response.

In summary, a multiple-coil device can control destructive and constructive interference through a set of independently controlled coils and can yield spatial and temporal control of the magnetic and induced electric fields thus addressing major unmet needs for neuromodulation. The device utilizes at least three coils each oriented in a different direction and driven by at least three independent signals. Individual fields from the at least three coils are combined to create a resultant field, and this resultant field may take advantage of destructive and constructive interference between the individual fields.

The various embodiments described above may be implemented using circuitry, firmware, and/or software modules that interact to provide particular results. One of skill in the arts can readily implement such described functionality, either at a modular level or as a whole, using knowledge generally known in the art. For example, the flowcharts and control diagrams illustrated herein may be used to create computer-readable instructions/code for execution by a processor. Such instructions may be stored on a non-transitory computer-readable medium and transferred to the processor for execution as is known in the art. The structures and procedures shown above are only a representative example of embodiments that can be used to provide the functions described hereinabove.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

The foregoing description of the example embodiments has been presented for the purposes of illustration and description. It is not intended to be exhaustive or to limit the embodiments to the precise form disclosed. Many modifications and variations are possible in light of the above teaching. Any or all features of the disclosed embodiments can be applied individually or in any combination are not meant to be limiting, but purely illustrative. It is intended that the scope of the invention be limited not with this detailed description, but rather determined by the claims appended hereto.

The invention claimed is:

1. A neuromodulator, comprising:
one or more coil sets, each of the one or more coil sets comprising three coils aligned to produce magnetic and electric fields in three different directions;
a plurality of conductors that couple the coils of the one or more coil sets to one or more input signals such that each of the coils is independently activated via an individually selectable current applied through the conductors, the individual activation creating a resultant field that is a combination of the magnetic and electric fields in the three different directions for each of the one or more coil sets; and
a controller coupled to the plurality of conductors, the controller operable to input a plurality of signals to the one or more coils sets to combine the magnetic and electric fields from each of the coils of the one or more coil sets, wherein the controller is further configured to control phases and amplitudes of each of the plurality of signals and induce at least one of constructive and destructive interference between the magnetic and electric fields inside an organic tissue.

2. The neuromodulator of claim 1, wherein the three different directions are orthogonal.

3. The neuromodulator of claim 1, further comprising a sensor configured to be located proximate a target region of the organic tissue, the sensor measuring an effect of the resultant field on the organic tissue and providing a feedback signal to the controller, the feedback signal used for closed-loop control of the resultant field.

4. The neuromodulator of claim 1, wherein the three coils of each of the one or more coil sets are scaled such that a target volume of the resultant field is 1.5-5 mm$^3$.

5. The neuromodulator of claim 1, further comprising a treatment surface that is configured for transcutaneous treatment of the organic tissue, and wherein the one or more coil sets comprise an array of coil sets embedded beneath the treatment surface.

6. The neuromodulator of claim 5, further comprising heat sinks between individual coils sets of the array.

7. The neuromodulator of claim 3, wherein the constructive and destructive interference is guided by the closed-loop control of the resultant field.

8. The neuromodulator of claim 1, wherein the individually selectable currents are selected to steer the resultant field to address specific regions of the organic tissue.

9. A neuromodulation system, comprising:
one or more coil sets, each of the coil sets comprising three coils aligned to produce magnetic and electric fields in three different directions; and
a controller coupled to the one or more coil sets, the controller operable to independently activate each of the coils via individually selectable currents causing each of the coils to emit an individual field, the individual fields creating a resultant field that is a combination of the magnetic and electric fields in the three different directions for each of the one or more coil sets, wherein the controller is further configured to control phases and amplitudes of each of the individually selectable currents and induce at least one of constructive and destructive interference between the magnetic and electric fields inside an organic tissue.

10. The neuromodulation system of claim 9, wherein the three different directions are orthogonal.

11. The neuromodulation system of claim 9, wherein the three coils of the one or more coil sets each have a first side connected to a common line of a plurality of conductors, wherein a second side of each of the three coils are coupled to separate lines of the plurality of conductors.

12. The neuromodulation system of claim 9, further comprising a sensor configured to be located proximate a target region of the organic tissue, the sensor measuring an effect of the resultant field on the organic tissue and providing a feedback signal to the controller, the feedback signal used for closed-loop control of the resultant field within the organic tissue.

13. The neuromodulation system of claim 7, wherein the three coils of each of the one or more coil sets are scaled such that a target volume of the resultant field is 1.5-5 mm$^3$.

14. A method comprising:
independently applying three or more individually selectable currents to three or more coils aligned to produce magnetic and electric fields in at least three different directions;
in response to the application of the currents, creating a resultant field that is a combination of the magnetic and electric fields in three different directions for each of the three or more coils;
applying the resultant field to neuromodulate organic tissue;
controlling phases and amplitudes of each of the individually selectable currents and causing at least one of constructive and destructive interference between the magnetic and electric fields in response to the application of the currents.

15. The method of claim 14, further comprising:
measuring a response of the organic tissue to the resultant field; and
using the response to modify the resultant field to achieve a target response.

16. The method of claim 15, wherein the response is measured via at least one of magnetic resonance imaging, functional magnetic resonance imaging, and electroencephalogram.

17. The method of claim 15, wherein measuring the response comprises measuring changes in a material property of the organic tissue.

18. The method of claim 17, wherein the material property comprises at least one of temperature, electrical conductivity, and chemical balance.

19. The method of claim 15, wherein the resultant field is applied to neurostimulate the organic tissue.

20. The method of claim 15, wherein the resultant field is applied to neurosuppress the organic tissue.

* * * * *